United States Patent
Ye et al.

(10) Patent No.: US 6,727,492 B1
(45) Date of Patent: Apr. 27, 2004

(54) CAVITY RINGDOWN SPECTROSCOPY SYSTEM USING DIFFERENTIAL HETERODYNE DETECTION

(75) Inventors: Jun Ye, Louisville, CO (US); John L. Hall, Boulder, CO (US)

(73) Assignees: Regents of the University of Colorado, Boulder, CO (US); The United States of America as represented by the Secretary of Commerce, Washington, DC (US)

( * ) Notice: Subject to any disclaimer, the term of this patent is extended or adjusted under 35 U.S.C. 154(b) by 483 days.

(21) Appl. No.: 09/759,729

(22) Filed: Jan. 12, 2001

Related U.S. Application Data

(60) Provisional application No. 60/191,574, filed on Mar. 23, 2000, and provisional application No. 60/175,956, filed on Jan. 13, 2000.

(51) Int. Cl.$^7$ ................................................. G01J 1/04

(52) U.S. Cl. .............................................. 250/227.18

(58) Field of Search ........................... 250/343, 227.18; 356/346, 349, 437, 440, 439, 432

(56) References Cited

U.S. PATENT DOCUMENTS

| | | | |
|---|---|---|---|
| 4,193,690 A | 3/1980 | Levenson et al. | |
| 4,817,101 A | 3/1989 | Wyeth et al. | |
| 4,905,244 A | 2/1990 | Wyeth et al. | |
| 5,528,040 A | 6/1996 | Lehmann | |
| 5,835,231 A | 11/1998 | Pipino | |
| 5,973,864 A | 10/1999 | Lehmann et al. | |
| 5,986,768 A | 11/1999 | Pipino | |
| 6,094,267 A | * 7/2000 | Levenson et al. | 356/453 |
| 6,097,555 A | 8/2000 | Lehmann et al. | |
| 6,233,052 B1 | * 5/2001 | Zare et al. | 356/437 |

OTHER PUBLICATIONS

Kastler, "Atomes a l'Interieur d'un Interferometre Perot–Fabry," Applied Optics, vol. 1, No. 1, 01–62, pp 17–24.

Cerez, Brillet, Man–Picho, & Felder, "He–Ne Lasers Stabilized by Saturated Absorption in Iodine at 612 nm," IEEE Transactions on Instrumentation and Measurement, vol. IM–29, No. 4, 12–80 , pp 352–354.

Drever, Hall, Kowalski, Hough, Ford Munley, & Ward "Laser Phase and Frequency Stabilization Using an Optical Resonator," Applied Phys. B 31, 1983, pp 97–105.

Anderson, Frisch & Masser, "Mirror Reflectometer based on Optical Cavity Decay Time," Applied Optics, vol. 23, No. 8 , Apr. 15, 1984, pp 1238–1245.

O'Keefe, & Deacon, Cavity Ring–down Optical Spectrometer for Absorption Measurements using Pulsed Laser Sources, Rev. Sci. Instrum., vol. 59, No. 12, 12–88, pp 2544–2551.

Ma Long–Sheng, & Hall, "Optical Heterodyne Spectroscopy Enhanced by an External Optical Cavity: Toward Improved Working Standards," IEEE Journal of Quantum Electronics, vol. 26, No. 11, 11–90, pp 2006–2012.

Levenson, Paldus, Spence, Harb, Harris Jr., Zared, "Optical Heterodyne Detection in Cavity Ring–down Spectroscopy," Chemical Physics Letters 290, 1998, pp 335–340.

(List continued on next page.)

Primary Examiner—Tu T. Nguyen
(74) Attorney, Agent, or Firm—Charles E. Rohrer

(57) ABSTRACT

An ac technique for cavity ringdown spectroscopy permits $1 \times 10^{-10}$ absorption sensitivity with microwatt light power. Two cavity modes are provided temporally out of phase such that when one mode is decaying, the other mode is rising. When one of the modes probes intra-cavity absorption of a sample gas, heterodyne detection between the two modes reveals dynamic time constants associated with the cavity and the cavity plus intra-cavity absorption. The system and method provides a quick comparison between on-resonance and off-resonance modes and enables sensitivities that approach the shot-noise limit.

56 Claims, 5 Drawing Sheets

OTHER PUBLICATIONS

Ye, Long–Sheng Ma, & Hall, "Ultrasensitive Detections in Atomic and Molecular Physics: Demonstration in Molecular Overone Spectroscopy," J. Opt. Soc. Am. B, vol. 15, No. 1, 01–98, pp 6–15.

Pipino, "Ultrasensitive Spectroscopy with a Miniature Optical Resonator," Physical Review Letters, vol. 83, No. 15, Oct. 11, 1999, pp 3093–3096.

Ye, & Hall, "Cavity Ring–down Heterodyne Spectroscopy: High Sensitivity with Microwatt Light Power," Physical Review A, vol. 61, May 17, 2000, No. 061802, pp 1–4.

Ye, Long–Sheng Ma, & Hall, "High–Resolution Frequency Standard at 1030 nm for Yb:YAG Solid–State Lasers," J. Opt. Soc. Am. B, vol. 17, No. 6, Jun. 2000, pp 927–931.

* cited by examiner

T(normalized to cavity field (1/e) decay time)

CAVITY RINGDOWN SPECTROSCOPY SYSTEM USING DIFFERENTIAL HETERODYNE DETECTION

This application claims the benefit of U.S. Provisional Applications No. 60/175,956 filed Jan. 13, 2000 and No. 60/191,574 filed Mar. 23, 2000.

FIELD OF THE INVENTION

This invention relates to the field of absorption spectroscopy and, in particular, to a cavity-ringdown system for the determination of ringdown rates by optical heterodyne detection.

BACKGROUND OF THE INVENTION

Traditional spectroscopic methods are limited in sensitivity to approximately one part per ten thousand ($1:10^4$) to one part per hundred thousand ($1:10^5$). The sensitivity limitation arises from instabilities in light-source intensity translated into noise in the absorption signal.

The use of optical resonators for enhancing absorption contrast is described by Kastler ("Atomes à l'Intérieur d'un Interféromètre Perot-Fabry," Appl. Opt. 1, 1 (1962) pp 17–24) and implemented by Cerez et, al. ("He-Ne Lasers Stabilized by Saturated Absorption in Iodine at 612 nm," IEEE Trans. Instrum. & Meas. 29, 4 (1980) pp 352–354) and Ma et. al. ("Optical Heterodyne Spectroscopy Enhanced by an External Optical Cavity: Toward Improved Working Standards," IEEE J. Quan. Electron. 26, 11 (1990) pp 2006–2012). Cavity Ring-Down Spectroscopy (CRDS), first described by O'Keefe and Deacon in "Cavity ring-down optical spectrometer for absorption measurements using pulsed laser sources," in Rev. Sci. Instrum. 59, 12 (1988): pp 2544–2551, allows absorption sensitivities of $1 \times 10^{-7}$. The applications of CRDS include measurement of ultra-slow reflector velocities, atmospheric sensing, detection of trace species in gas-phase environments, absolute determination of absorption-band strength and/or species concentration, analysis of combustion and plasma dynamics, study of chemical kinetics (such as radical reactions and internal vibration redistribution), and characterization of optical cavities and high-reflectivity mirror coatings. Recently, CRDS has been applied to surface and condensed matter (Pipino, "Ultrasensitive Surface Spectroscopy with a Miniature Optical Resonator," Phys. Rev. Lett. 83, 15 (11 Oct. 1999) pp 3093–3096), thus permitting a wide range of novel fundamental investigations.

In a CRDS system, a sample (absorbing material) is placed in a high-finesse stable optical resonator or ringdown cavity. The light completes many roundtrips through the intra-cavity absorber, effectively increasing the interaction length by 2·Finesse/$\pi$. Light admitted into the ringdown cavity circulates back and forth multiple times setting up standing waves having periodic spatial variations. Light exiting the ringdown cavity is proportional to the intra-cavity light intensity.

The radiant energy stored in the ringdown cavity decreases in time (rings down). For an empty cavity, the stored energy follows an exponential decay characterized by a ringdown rate that depends only on the reflectivity of the mirrors, the separation between the mirrors and the speed of light in the cavity. If a sample is placed in the resonator, the ringdown is accelerated. Information about intra-cavity gas absorption is obtained by measuring the change of decay associated with the cavity field. An unknown absorption coefficient is compared to known mirror losses. The mirror losses may have a magnitude similar to the unknown absorption coefficient in order to reduce background detection, thus enhancing contrast between the unknown absorption coefficient and the background (i.e., mirror losses). An absorption spectrum for the sample is obtained by plotting the reciprocal of the ringdown time T or the decay constant $1/\tau$ versus the wavelength $\lambda$ of the incident light.

U.S. Pat. No. 5,528,040 describes a CRDS system in which the decay rate of the ringdown cavity cell is calculated from a signal produced by a photodetector that is responsive to radiation resonated by the cell. The calculated decay rate is used to determine the level of trace species in the sample gas. The method measures cavity ringdown using a continuous wave laser. The cavity transmitted power is used to monitor the intracavity absorption. Lacking an efficient differential comparison mechanism, intensity noise of the diode laser used in the method places substantial limit on the achievable absorption sensitivity.

U.S. Pat. Nos. 5,986,768 and 5,835,231 describe elegant setups of high finesse optical resonators that permit measurement of absorption using evanescent waves to provide spatial resolution. However, the technique employed is the commonly used single beam cavity ringdown.

In CRDS, a pulsed operation produces an abrupt termination of the cavity input field, which permits a measurement of the exponential decay curve of the cavity-transmitted power. Intensity fluctuations of the incident light are not related to the ringdown rate in the ringdown cavity and thus, they do not directly affect the CRDS measurement. Thus, this cavity ringdown method avoids the noise in the light source. However, residual fluctuations in the apparent cavity loss prevent this method from achieving the performance suggested by fundamental noise limits. For example, if CRDS were only limited by shot-noise inherent in any light beam due to the quantum nature of the photons constituting the light beam, the achievable sensitivity would be in the range of $10^{-14}$ cm$^{-1}$ Hz$^{-\frac{1}{2}}$.

Various improvements to CRDS are well known. For example, U.S. Pat. No. 5,528,040 describes a laser-diode source for CRDS. The diode laser is optically locked using controlled optical feedback from a reference cavity to improve the coupling of light into the ringdown cavity. U.S. Pat. No. 6,084,682 describes a CRDS system that uses separate sampling and locking( light beams. The sampling and locking beams are provided with different wavelengths. U.S. Pat. No. 5,912,740 describes a ring resonant cavity that eliminates feedback into the light source. The absence of feedback to the light source leads to reduced frequency fluctuations, improved light-cavity coupling, reduced baseline noise, and increased absolute sensitivity. U.S. Pat. No. 5,815,277 describes an acousto-optic modulator used to couple light into a CRDS resonant cavity. U.S. Pat. Nos. 6,097,555 and 5,973,864 describe utilizing Brewster's angle prism retro-reflectors.

There are two basic limitations to conventional CRDS. One of these limitations is due to the DC nature of CRDS. For example, two decay-ti me measurements are made, one for an empty cavity and the other for a cavity containing a sample. The difference between the two measurements contains useful information. However, when there is a large time difference between the two measurements, slow drift and various noise factors contaminate the data.

Another limitation of CRDS is the requirement that a CRDS detector have a large dynamic range to record data. Typically, a lower portion of the exponential CRDS decay curve is masked by instrument noise because insufficient power is available for the decay curve to be distinguishable from electronic noise.

Accurate measurements of small signal changes with a varying background signal can be achieved with a precise signal-extraction method and averaging. Modulation techniques are typically employed to distinguish decay-time measurements from background signals so that any drifts and noise in the background can be removed. In "Ultrasensitive detections in atomic and molecular physics: demonstration in molecular overtone spectroscopy," J. Opt. Soc. Am. B 15, 1, pp 6–15 (1998), which is hereby incorporated by reference, a frequency-modulation technique enables shot noise limited absorption sensitivity in sub-Doppler resolution. On-resonance and off-resonance information are compared at a radio-frequency (RF) rate, which is located away from the laser-intensity noise spectrum.

Ye et al. ("Ultrasensitive Detection in Atomic and Molecular Physics: Demonstration in Molecular Overtone Spectroscopy", Journal of the Optical Society of America B, 15, 1, (January 1998), pp. 6–15) teaches a heterodyne technique building on spectroscopic techniques employing frequency modulation (FM) detection.

Levenson et. al. ("Optical heterodyne detection in cavity ring-down spectroscopy," Chem. Phys. Lett. 290 (1998) pp 335–340) describes a heterodyne technique used to superimpose a large local-oscillator field onto a decay field so that the resultant beat frequency is only light-noise limited.

U.S. Pat. No. 6,094,267 describes an optical heterodyne detection technique that improves the detection sensitivity of a CRDS system such that the sensitivity approaches the shot-noise limit. A local-oscillator signal and a signal wave are coupled into a ringdown cavity containing a sample. The local-oscillator signal and the signal wave have different frequencies. To perform the ring-down measurement, the signal wave is interrupted, such as by chopping the wave or changing the signal frequency. An exponentially decaying ringdown signal output from the cavity is combined with the uninterrupted local-oscillator signal to produce a heterodyne beat frequency. However, this technique does not offer the possibility of a quick comparison of on-resonance and off-resonance information, which is key to achieve Quantum noise limited sensitivity. Also, this technique still requires recording the entire ringdown decay curve, which needs a substantial dynamic range to record accurately the decay curve.

Unfortunately, the above adaptations are not well designed to measure exponentially decaying waveforms. In particular, these techniques do not work well for signal detection in CRDS. It is desirable to employ a single technique that simultaneously addresses the two basic limitations of CRDS. It is also desirable to provide a method that approaches the fundamental quantum-noise limit in cavity-enhanced linear spectroscopy.

SUMMARY OF THE INVENTION

An object of the present invention is to provide a CRDS system that is substantially immune to slow drift and various noise factors that typically contaminate data, and therefore enable a true quantum noise limited is detection sensitivity.

Another object of the invention is to provide a CRDS system that reduces the dynamic range of a CRDS detector required to accurately record data.

The present invention compares two slightly different time constants. One time constant is associated with an empty cavity. The other time constant is associated with cavity loss plus an additional loss. Using cavity filtering and an intensity-stabilized laser, it is possible to approach (within a factor of four) the fundamental quantum-noise limit in cavity-enhanced linear spectroscopy.

The invention uses heterodyne detection of two modes having a relative frequency offset that are chopped out of phase and coupled into a resonating cavity. One of the modes may be tuned to an absorption line of a sample gas in the cavity. In a first half-cycle, a heterodyne-beat signal results from one mode that is coupled into the cavity (and thus, rising exponentially in intensity) beating against a second mode that has been switched off (and thus, is diminishing exponentially in intensity). In a second half-cycle, the first mode is switched off and the second mode is switched on. Absorption of one of the modes by the sample gas is easily detected by observing the difference between adjacent half-cycles of the heterodyne beat signal.

DESCRIPTION OF THE PREFERRED EMBODIMENTS

Figure 1:
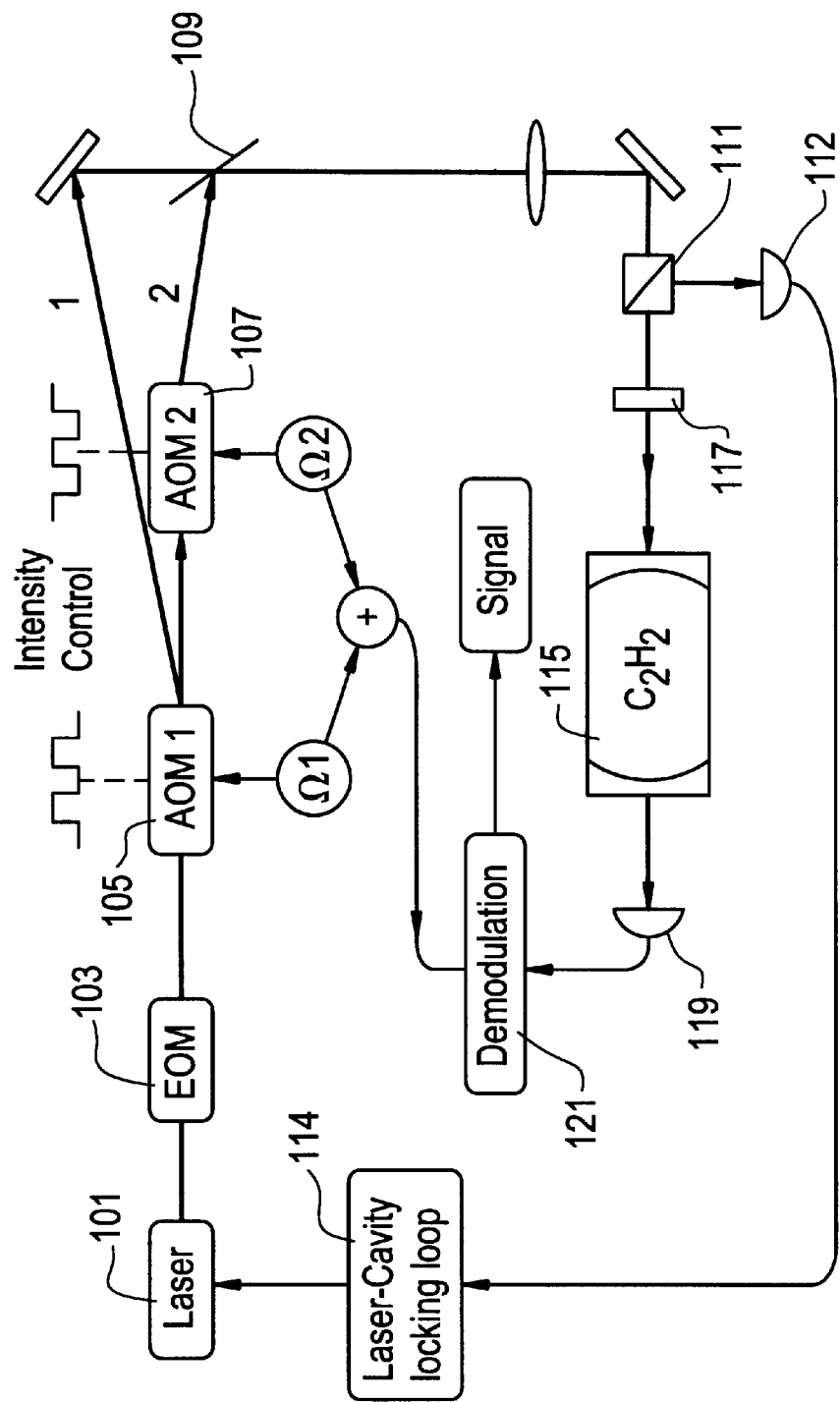
FIG. 1 shows one embodiment for a chopped heterodyne CRDS system. Two acousto-optic modulators provide a frequency offset between two modes that are chopped out of phase such that at any time, only one mode enters a cavity containing a sample gas. The laser can be locked onto the cavity, since there is always one mode entering the cavity. A heterodyne beat between the two modes at a cavity output is demodulated with respect to the known frequency offset to produce a decay signal. One of the two modes interacts with the intra-cavity molecules while the other one is tuned off resonance.

FIG. 1 is an illustration of an apparatus of the present invention. An intensity-stabilized continuous-wave (cw) laser 101 generates a beam that is provided with RF sidebands by an electro-optic modulator (EOM) 103. The beam is then split by a pair of acousto-optic modulators (AOM) 105 and 107. The AOMs 105 and 107 provide a 1.3-GHz relative frequency offset between the pair of split beams. The offset is preferably selected so that both beams can resonate within a high-finesse cavity, ref. no. 115. In this case, the cavity 115 has a free-spectral range of 318.34 MHz. Thus, the 1.3-GHz offset corresponds to a separation of four mode orders. The cavity 115 has a finesse of approximately 90,000.

The beams are combined at a beam splitter 109 and coupled into the cavity. However, the AOMs 105 and 107 chop the intensities of the beams out of phase such that only one beam is coupled into the cavity at any time. Although the beams are switched periodically at the cavity input, a detector 112 that monitors the cavity reflection uses the Pound-Drever-Hall technique (such as described in "Laser phase and frequency stabilization using an optical resonator," Appl. Phys. B 31, 97 (1983)) to maintain the laser/cavity lock using the RF sidebands generated by the EOM 103. This is possible because there is always one beam that is in resonance with the cavity. A polarized beam splitter 111 and a quarter-wave plate 117 are used to steer the reflected beam onto the photodetector 112 that provides a feedback signal to a laser-cavity locking loop 114.

The beam coupled into the cavity 115 produces a rising mode that rises exponentially while the previously coupled beam decays exponentially within the time scale of the cavity ringdown. The transmitted signal from the cavity 115 has a heterodyne beat waveform occurring between the rising and decaying modes inside the cavity 115. This output signal is detected by an avalanche photodiode 119. A demodulation unit 121 accepts an electrical signal from the avalanche photodiode 119 and the 1.3 GHz frequency-offset signal from the AOMs 105 and 107. Demodulating or otherwise downconverting the known carrier frequency (1.3 GHz) of the beat waveform to baseband reveals the heterodyne beat amplitude. The beat amplitude contains information about the dynamic variation between the modes, and thus the intra-cavity absorption signal.

Figure 2A:
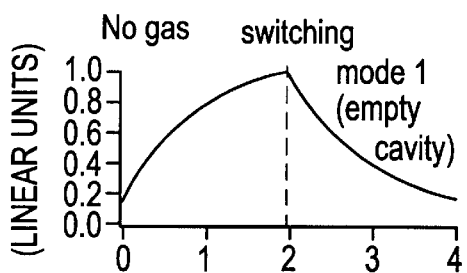
FIG. 2A shows a demodulated ringdown curve for a first mode in an empty cavity.
Figure 2E:
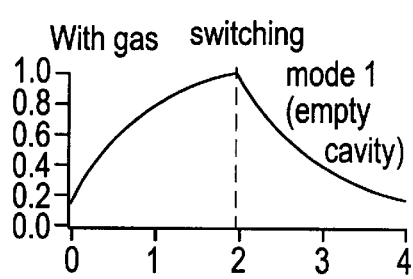
FIG. 2E shows a demodulated ringdown curve for a first mode, which is tuned to an off-resonance of a sample gas in the cavity.
Figure 2B:
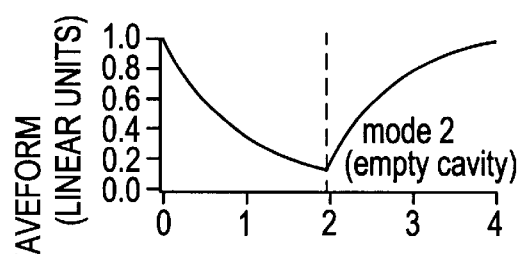
FIG. 2B shows a demodulated ringdown curve for a second mode in the empty cavity.

FIG. 2A and FIG. 2B show relative variations of the two modes in an empty cavity. In the first chopping cycle shown, mode 1 is switched into the cavity 115 and thus, rises exponentially. At the same time, mode 2 is switched off and thus, decays exponentially. At the second chopping cycle, mode 1 is switched off (and thus, decays exponentially) while mode 2 is switched into the cavity 115 (and thus, rises exponentially).

Figure 2F:
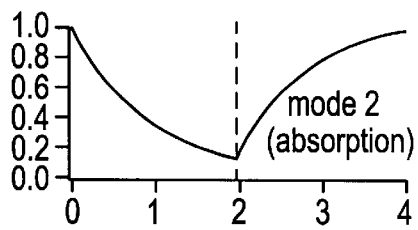
FIG. 2F shows a demodulated ringdown curve for a second mode, which is tuned to a molecular resonance of the sample gas in the cavity.
Figure 2C:
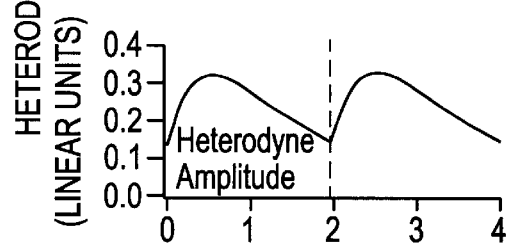
FIG. 2C shows a heterodyne-beat amplitude of the first and second modes measured at the output of the empty cavity.

FIG. 2C shows a heterodyne-beat amplitude of the modes measured at the output of the empty cavity. A heterodyne-beat waveform that occurs between mode 1 and mode 2 is demodulated relative to the 1.3-GHz frequency offset to produce the heterodyne-beat amplitude. The heterodyne-beat amplitude contains information about the dynamic variation of the modes. In an empty cavity, the heterodyne-amplitude waveform remains unchanged for adjacent chopping cycles. FIG. 2D shows a difference signal for the heterodyne amplitude between adjacent chopping cycles.

FIG. 2E and FIG. 2F show relative variations of the two modes in a cavity containing a sample gas. Mode 1 is not absorbed by the gas. However, mode 2 is tuned to a molecular resonance of the gas and is absorbed. The system exhibits two slightly different time constants associated with the two modes. The rise and decay curves shown in FIG. 2E are similar to the curves shown in FIG. 2A. In FIG. 2F, the absorption affects both the rise and decay curves.

Figure 2G:
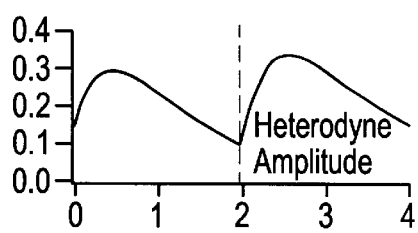
FIG. 2G shows a heterodyne-beat amplitude of the first and second modes measured at the output of the cavity containing the sample gas.
Figure 2D:
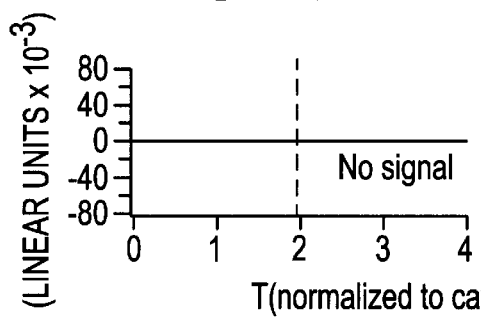
FIG. 2D shows a difference signal, which is a difference of the heterodyne-beat signal between adjacent half chopping cycles. In the absence of differential absorption between the two modes, the difference signal is zero.
Figure 2H:
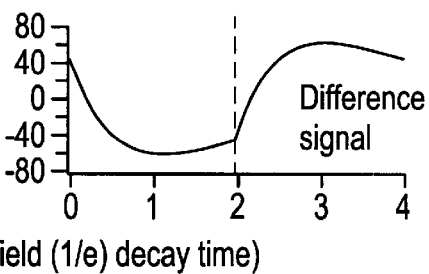
FIG. 2H shows a difference signal, which is a difference of the heterodyne-beat signal between adjacent chopping cycles. The difference signal is non-zero because the second mode experiences absorption due to the gas whereas the first mode does not.

The heterodyne amplitude shown in FIG. 2G is slightly different between adjacent chopping cycles. This difference is related to the intra-cavity absorption. A non-zero difference signal resulting from the asymmetric heterodyne amplitude shown in FIG. 2G is shown in FIG. 2H.

In a preferred embodiment, the period of the chopping cycle may be selected to approximately match the decay time 1/e of the empty cavity. This embodiment enables a quick comparison of on-resonance and off-resonance information and suppresses technical noises associated with the light and the cavity. Since each ringdown waveform is processed within one chopping period (which is on the order of 1/e decay time), this reduces the dynamic range needed to record the signal by several decades. Thus, the present invention makes full use of the resolution of the digitization process.

The characteristic time constant $\tau_{cav}$ (i.e., the 1/e-decay time) associated with the mode dynamics of a field applied to an empty cavity can be expressed by a round-trip loss $L_{cav}$ and a round-trip time $t_{roundtrip}$ of the light:

$$\tau_{cav} = \frac{2t_{roundtrip}}{L_{cav}} \quad (1)$$

This time constant expression for an empty cavity is equivalent to an expression for a cavity mode that is far detuned from the medium resonance.

The time constant for a mode that is tuned to an absorption peak of the medium can be expressed by:

$$\tau_{abs} = \frac{2t_{roundtrip}}{L_{cav} + A} \quad (2)$$

where A is the round-trip absorption of the intra-cavity medium.

In the intensity-chopping scenario described with reference to FIG. 1 and FIG. 2A to 2H, mode 1 corresponds to an empty-cavity or off-resonance mode and mode 2 corresponds to an on-resonance mode that experiences intra-cavity absorption. During a first half-period $[0, \Delta t/2]$, mode 1 is switched on and mode 2 is switched off. Field amplitudes $E_1$ and $E_2$ for modes 1 and 2, respectively, are expressed by:

$$E_1 = c_1[1 + \exp(-\Delta t/2\tau_{cav}) - \exp(-t/\tau_{cav})]; \quad (3)$$

$$E_2 = c_2\exp(-t/\tau_{abs});$$

where $c_1$ and $c_2$ are amplitude coefficients.

During a second half-period [Δt/2, Δt], mode 1 is switched off and mode 2 is switched on. The demodulated heterodyne-beat waveform is expressed by the product of the field amplitudes $E_1$ and $E_2$. A comparison of the heterodyne-beat amplitudes for two neighboring half-cycles can be expressed by a difference equation:

$$(E_1 E_2)_{[0, \Delta t/2]} - (E_1 E_2)_{[0, \Delta t/2]} = \quad (4)$$

$$c_1 c_2 \left[ \left(1 + e^{-\frac{\Delta t}{2\tau_{cav}}}\right) e^{-\frac{t}{\tau_{abs}}} - \left(1 + e^{-\frac{\Delta t}{2\tau_{abs}}}\right) e^{-\frac{t}{\tau_{cav}}} \right]$$

In FIGS. 2A to 2H, the chopping period Δt is selected to be $4\tau_{cav}$ and the time axes are normalized to $\tau_{cav}$. In an empty cavity, the switched waveforms of mode 1 and mode 2 are symmetric, resulting in a uniform heterodyne-beat amplitude between neighboring half-cycles. When mode 1 and mode 2 experience different cavity losses, the resulting heterodyne-beat amplitude is asymmetric with respect to neighboring half-cycles. Differences between neighboring half-cycles indicate the amount of additional absorption.

The sensitivity of the method of the invention can be expressed with respect to equations (3) and (4). The difference signal shown in equation (4) can be expressed by:

$$i_{signal} \approx \eta \frac{2}{\sqrt{2}} P_0 \left[ e^{-\frac{t}{\tau_{abs}}} - e^{-\frac{t}{\tau_{cav}}} \right] = -\eta \sqrt{2} P_0 e^{-\frac{t}{\tau_{cav}}} \left[ 1 - e^{-\frac{1}{\tau_{abs}} - \frac{1}{\tau_{cav}}} \right] \quad (5)$$

$$= -\eta \sqrt{2} P_0 \left( \frac{1}{\tau_{abs}} - \frac{1}{\tau_{cav}} \right) \cdot t \cdot e^{-\frac{t}{\tau_{cav}}}$$

In equations (3&4), $c_1 = c_2 = \sqrt{P_0}$, and light is converted to a photo current according to $i = \eta \cdot P$, where η is the detector responsivity (A/W). The demodulation beat current is $\eta \cdot 2 E_1 E_2 / \sqrt{2}$. In this case the small absorption limit $\tau_{cav} \approx \tau_{abs}$ is provided and $\Delta t / \tau_{cav} \geq 10$. Since the beat amplitude is maximum when $E_1 = E_2$, then $\exp(-t/\tau_{cav}) \approx \frac{1}{2}$ and $t = \tau_{cav} \ln 2$. Thus, $i_{signal}$ can be expressed by:

$$i_{signal} = -\eta \sqrt{2} P_0 \tau_{cav} \frac{\ln 2}{2} \cdot \frac{A}{2 t_{roundtrip}} = -\eta P_0 \frac{\ln 2}{\sqrt{2}} \cdot \frac{A}{L_{cav}}. \quad (6)$$

The shot noise produced by the DC photo current, $$i_{DC} = \eta \cdot 2 \left( \frac{\sqrt{P_0}}{2} \right)^2 = \eta P_0 / 2, \text{ is } i_{noise} = \sqrt{2 e B \cdot \eta P_0 / 2},$$

where e is the electron charge and B is the detection bandwidth. The resultant signal-to-noise ratio (S/N) is:

$$\left| \frac{i_{signal}}{i_{noise}} \right|_{shot\ noise} = \sqrt{\frac{\eta P_0}{eB}} \frac{\ln 2}{\sqrt{2}} \frac{A}{L_{cav}}. \quad (7)$$

In terms of noise-equivalent sensitivity of single-pass integrated absorption, we set S/N=1 and:

$$\left( \frac{A}{2} \right)_{min} = \frac{\sqrt{2}}{\ln 2} \sqrt{\frac{eB}{\eta P_0}} \frac{L_{cav}}{2} = \frac{\sqrt{2}}{\ln 2} \sqrt{\frac{eB}{\eta P_0}} \frac{\pi}{Finesse}. \quad (8)$$

The sensitivity expression of equation (8) is similar to equation (3) in "Ultrasensitive detections in atomic and molecular physics: demonstration in molecular overtone spectroscopy," Ye et. al., J. Opt. Am. B, 15, 1 (1998) pp 6–15, except for a factor of approximately 2. This similarity is expected because both techniques are shot-noise limited. The difference is due to some of the carrier power being converted to the sidebands in cavity-enhanced frequency-modulation spectroscopy. This conversion leads to a slight loss of sensitivity for a fixed total power.

In one embodiment of the present invention, a Yb:YAG laser is used to probe acetylene gas inside a high-finesse cavity having a length of 46.9 cm. An intra-cavity gas pressure of a few mTorr may be used. A probing mode is tuned to a vibration overtone line $C_2H_2(3\nu_3)R(29)$ having a wavelength of 1031.6528 nm and an absorption coefficient of is $4 \times 10^{-6}$/Torr·cm. This system and its operation are described by Ye, et. al. in "High-resolution frequency standard at 1030 nm for Yb:YAG solid-state lasers," J. Opt. Soc. Am. B, 17, 6 (2000) pp 927–931, which is hereby included by reference.

The system operates with a beam-chopping frequency of 1.4 kHz (Δt~714 μs). The cavity transmission is received by an avalanche photodiode that couples a beat signal to an RF spectrum analyzer for demodulation.

Figure 3:
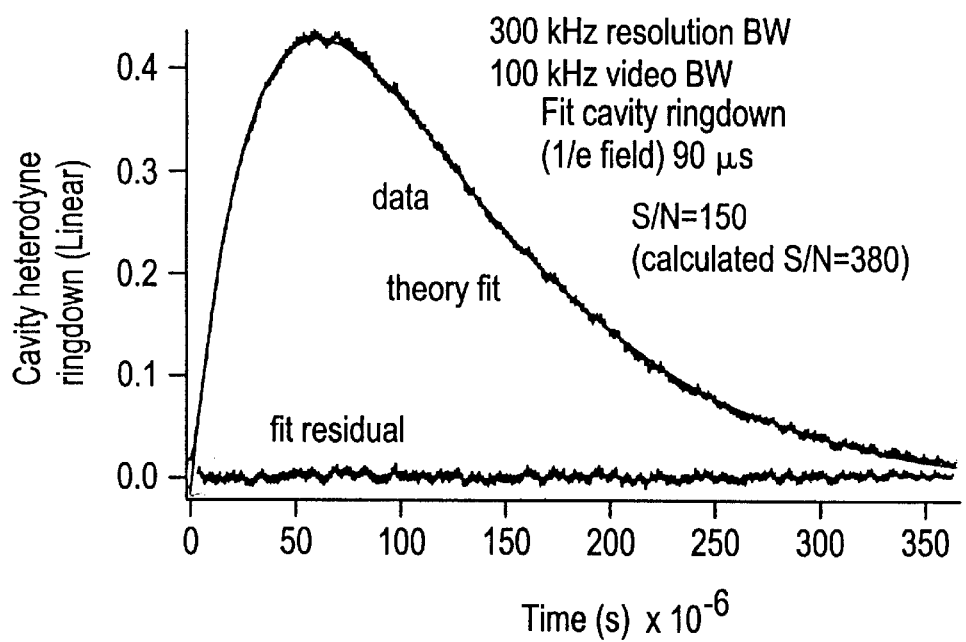
FIG. 3 shows a trace of a chopped ringdown curve for an empty cavity. The trace was obtained from a video output of an RF spectrum analyzer. A theoretical fit and the fit residual are also shown.

Empty-cavity finesse is measured by tuning both mode 1 and mode 2 out of the molecular resonance of the gas. FIG. 3 is a plot of a measured demodulated heterodyne-beat ringdown waveform along with a theoretical fit corresponding to the mathematical model derived previously herein. The mathematical model provides an excellent fit to the measured data and produces an estimated cavity ringdown (1/e) time of 90 μs. This results in a cavity linewidth of 3.5 kHz (FWHM) and a finesse of 90,000. Within a detection bandwidth of 173 kHz (resolution bandwidth of 300 kHz and video bandwidth of 100 kHz), the recovered signal-to-noise ratio is 150. The recovered signal-to-noise ratio is approximately two times smaller than the expected value, partly due to ringing noise of the spectrum analyzer's RF filter function, which is optimized for frequency-domain analysis. Smaller analyzer bandwidths were observed to increase distortion of the ringdown signal.

Figure 4:
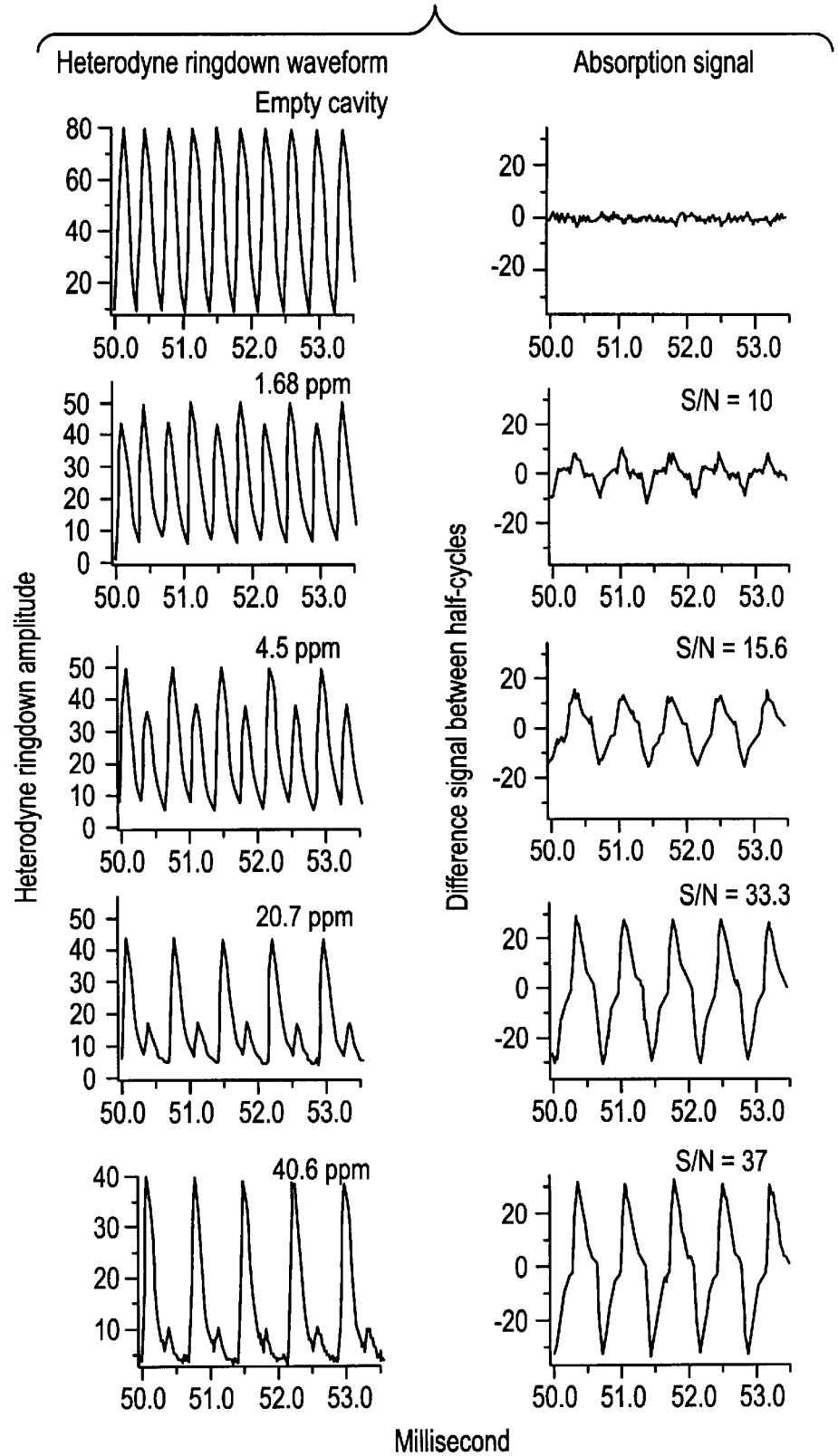
FIG. 4 shows five heterodyne-beat amplitudes (left column) that occur between two chopped cavity modes. Each of the heterodyne-beat amplitudes corresponds to a different intra-cavity absorption that affects one of the modes. Five absorption signals (right column) are also shown. Each of the absorption signals is a difference in beat amplitude of neighboring half cycles shown in the corresponding heterodyne-beat amplitudes.

When mode 2 is tuned to the center of the acetylene resonance, the ringdown waveform becomes asymmetric for adjacent half-cycles. FIG. 4 illustrates a set of ringdown beat waveforms corresponding to a set of different intra-cavity absorption levels, which are related to different intra-cavity gas pressures. Five different gas pressures were provided, including C zero pressure (i.e., empty cavity). FIG. 4 also shows a set of absorption waveforms derived from the ringdown beat waveforms. The absorption signals are generated by a difference between each ringdown beat waveform and a copy of the waveform that is shifted in time by a half chopping cycle.

In a single-pass absorption of $1.7 \times 10^{-6}$, the acquired signal to noise is 10 with a bandwidth of 173 kHz. The absorption sensitivity normalized to 1-s averaging time is $1.6 \times 10^{-6}$. At a steady state (i.e., no chopping), each mode has 3 μW ($P_0$) in the cavity transmission. The value of η of the avalanche photodiode is 0.3 A/W. The shot noise limited sensitivity of equation (8) is then approximately $1.2 \times 10^{-11}$ at 1-second averaging. However, since the avalanche photodiode has an excess noise factor of three, the expected minimum absorption sensitivity should be approximately $4 \times 10^{-11}$, which is a factor of four lower than this experimental result.

Figure 5A:
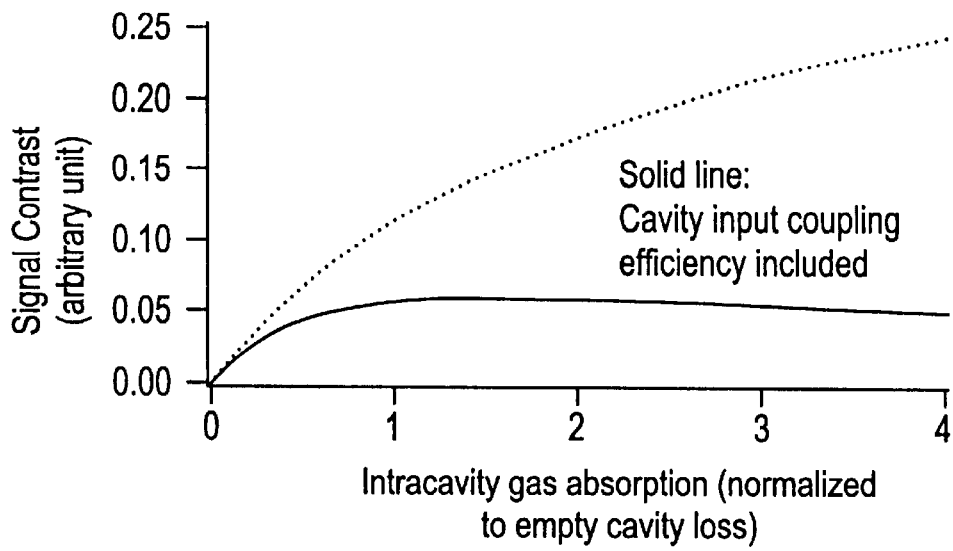
FIG. 5A shows a pair of curves representing signal-contrast versus intra-cavity molecular absorption. A solid line curve includes a change of cavity input coupling efficiency. A dotted line curve indicates no inclusion is of a change of cavity input coupling efficiency.

In FIG. 4, the absorption-signal amplitude does not increase linearly with respect to cavity absorption. FIG. 5A shows signal contrast against intra-cavity absorption normalized to the empty-cavity loss. The dotted line curve is calculated based on an assumption that the coupling power to mode 2 (the absorbing mode) is constant. However, since there is additional loss inside the cavity, the power coupling efficiency to the cavity changes and the available power for mode 2 decreases. Thus, for a fixed incident power, signal saturation occurs sooner, as shown by the solid line shown in FIG. 5A.

Figure 5B:
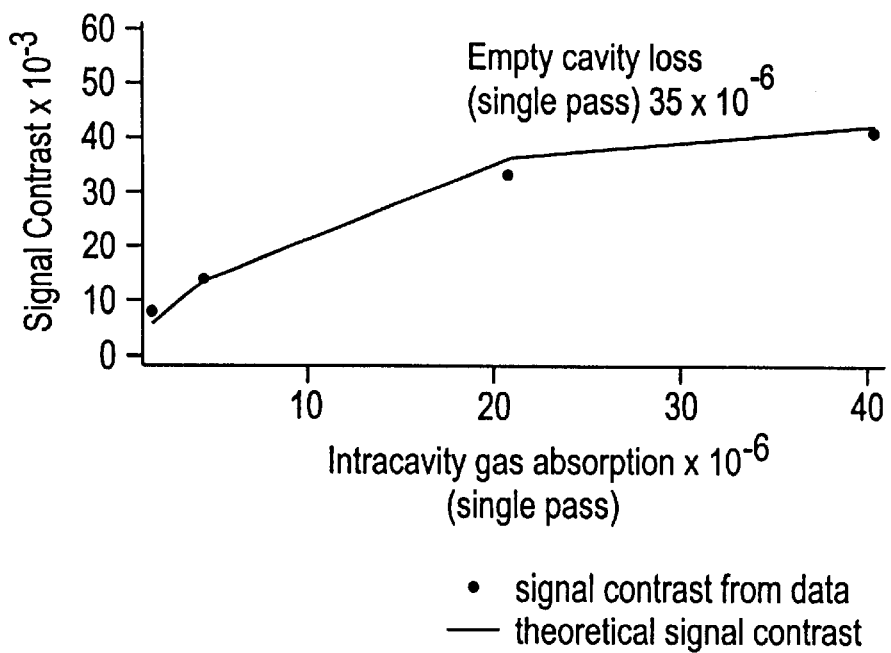
FIG. 5B shows a plot of signal contrast relative to intra-cavity absorption for experimental data and theory. The experimental data (taken from FIG. 4) shows signal saturation occurring when molecular absorption approached the empty-cavity loss, which in this case is $35 \times 10^{-6}$ for a single pass.

FIG. 5B illustrates saturation of the experimental data shown in FIG. 4. The model illustrated by FIG. 5A is used to fit the data plotted in FIG. 5B. A solution to the problem of saturation may include increasing the power input to the cavity as intra-cavity absorption increases. Another means for addressing the problem of saturation is to use faster chopping cycles.

The application of the present invention to CRDS enables shot noise limited detection for linear absorption measurements. There is excellent agreement between the experimental ringdown waveform and the theoretical models. Measurements made in the presence of $1 \times 10^{-6}$ intra-cavity absorption indicate a detection sensitivity of $1.6 \times 10^{-10}$ at a 1-s averaging time. Particular applications of the present invention include, but are not limited to, spectrum measurements made under conditions of Doppler or atmospheric-pressure broadening.

Although particular embodiments are described, improvements and adaptations to the embodiments may be provided without departing from the scope of the invention. Improvements may include basic operational changes, such as using faster chopping cycles. Improvements may include component changes, such as replacing the avalanche photodiode with a sensitive p-i-n diode in a resonant matching circuit. Adaptations may include stabilizing the laser on the cavity with a third mode that is off resonance and independent of the other two modes. The third mode can be left on continuously to maintain a lock while the first two modes are switched. The heterodyne-detection process can be adapted to filter out contributions from the third mode.

The foregoing discussion and the claims that follow describe the particular embodiments of the present invention discussed herein. Particularly with respect to the claims, it should be understood that changes may be made in particular embodiments without departing from the essence of the invention. In this regard, it is intended that such changes would still fall within the scope of the claimed invention. To the extent such revisions utilize the essence of the present invention, each naturally falls within the breadth of protection encompassed by this patent. This is particularly true for the present invention, since its basic concepts and understandings are fundamental in nature and can be broadly applied.

What is claimed is:

1. A cavity ringdown system capable of providing optical heterodyne detection of a ringdown signal including:
    an optical-signal generator capable of generating an optical beam comprising a plurality of modes, the modes being chopped out of phase with respect to a chopping cycle such that no more than one of the chopped modes is dominant in the output,
    an optical resonator optically coupled to the signal generator capable of receiving the optical beam, the resonator being capable of containing an intra-cavity absorber onto which at least one of the modes may be tuned, and
    a heterodyne detector coupled to the optical resonator, the heterodyne detector capable of receiving a plurality of the modes and demodulating a heterodyne-beat waveform between the modes to produce a heterodyne-beat amplitude, the heterodyne detector generating a difference signal of the heterodyne-beat amplitude between adjacent chopping cycles, which contains the information of intra-cavity absorption.

2. The cavity ringdown system recited in claim 1 wherein the optical-signal generator includes an intensity-stabilized continuous-wave laser.

3. The cavity ringdown system recited in claim 1 wherein the optical-signal generator includes a tunable cw laser.

4. The cavity ringdown system recited in claim 1 wherein the optical-signal generator includes an electro-optic modulator capable of providing RF sidebands to the optical beam.

5. The cavity ringdown system recited in claim 1 wherein the optical-signal generator includes a plurality of acousto-optic modulators capable of splitting the beam into a plurality of modes having a relative frequency offset.

6. The cavity ringdown system recited in claim 1 wherein the optical resonator is characterized by a free-spectral range and the optical-signal generator is adapted to generate modes having a frequency offset that is an integer multiple of the free-spectral range.

7. The cavity ringdown system recited in claim 1 wherein the optical-signal generator includes a chopping system capable of chopping the modes out of phase.

8. The cavity ringdown system recited in claim 7 wherein the chopping system includes a plurality of acousto-optic modulators.

9. The cavity ringdown system recited in claim 1 further comprising:
    a pre-fixed cavity resonance photodetector,
    a polarized beam splitter and a quarter-wave plate capable of steering the entire reflected optical beam from the optical resonator onto the pre-fixed photodetector, said photodetector optically coupled to the beam splitter, the photodetector capable of receiving the reflected optical beam and converting the received beam to an electrical signal, and
    a laser-cavity locking loop electrically coupled to the photophotodetector, the laser-cavity locking loop capable of receiving the electrical signal and generating a feedback signal to maintain a lock between the optical-signal generator and the optical resonator.

10. The cavity ringdown system recited in claim 9 wherein the lock between the optical-signal generator and the optical resonator is maintained using the Pound-Drever-Hall technique.

11. The cavity ringdown system recited in claim 9 wherein the optical-signal generator includes an electro-optic modulator capable of providing RF sidebands to the optical beam.

12. The cavity ringdown system recited in claim 9 wherein the optical-signal generator generates an off-resonance continuous mode that is processed by the laser-cavity locking loop to maintain a lock between the optical-signal generator and the optical resonator.

13. The cavity ringdown system recited in claim 12 wherein the heterodyne photodetector is adapted to filter out contributions of the continuous mode to the heterodyne-beat waveform.

14. The cavity ringdown system recited in claim 1 wherein the optical resonator is characterized by a decay time relative to an empty cavity, and the optical-signal generator chops the modes with respect to a chopping cycle suitable for the decay time.

15. The cavity ringdown system recited in claim 1 wherein the optical resonator is a high-finesse cavity.

16. The cavity ringdown system recited in claim 1 wherein the optical resonator is adapted to contain an intra-cavity sample gas.

17. The cavity ringdown system recited in claim 1 wherein the cavity reflection photodetector includes a p-i-n diode in a resonant matching circuit.

18. The cavity ringdown system recited in claim 1 wherein the heterodyne photodetector includes a suitable detector, such as an avalanche photodiode, resonant matched p-i-n photodiode or photomultiplier.

19. The cavity ringdown system recited in claim 1 wherein the heterodyne photodetection system includes an RF demodulation component.

20. The cavity ringdown system recited in claim 1 wherein the optical signal generator includes an adjustable power system capable of being responsive to increased intra-cavity absorption in the optical resonator for increasing power of the optical beam.

21. The cavity ringdown system recited in claim 1 wherein the optical signal generator includes an adjustable chopping system capable of being responsive to increased intra-cavity absorption in the optical resonator by decreasing duration of the chopping cycle.

22. A cavity ringdown system capable of providing optical heterodyne detection of a ringdown signal including:
   an optical source capable of generating an optical beam with a plurality of modes having a predetermined relative frequency offset between the modes,
   a high-finesse optical cavity capable of receiving the modes,
   a chopping system for chopping the modes out of phase such that only one dominant mode is coupled into the cavity at any time, and
   a heterodyne detector optically coupled to the cavity capable of detecting an optical signal coupled out of the cavity, the optical signal including the modes, which modes overlap to produce a heterodyne-beat waveform, the heterodyne detector including:
      a demodulation unit capable of demodulating the waveform to produce a heterodyne-beat amplitude, and
      a difference-signal analyzer coupled to the demodulator, the difference-signal analyzer capable of generating a difference signal from adjacent chopping cycles of the heterodyne-beat amplitude.

23. The cavity ringdown system recited in claim 22 wherein the optical source includes an intensity-stabilized continuous-wave laser.

24. The cavity ringdown system recited in claim 22 wherein the optical source includes a tunable cw laser.

25. The cavity ringdown system recited in claim 22 wherein the optical source includes an electro-optic modulator capable of providing RF sidebands to the optical beam.

26. The cavity ringdown system recited in claim 22 wherein the optical source includes a plurality of acousto-optic modulators capable of splitting the beam into a plurality of modes having a relative frequency offset.

27. The cavity ringdown system recited in claim 22 wherein the optical cavity is characterized by a free-spectral range and the optical source is adapted to generate modes having frequency offsets that are related to the free-spectral range.

28. The cavity ringdown system recited in claim 22 wherein the chopping system includes a plurality of acousto-optic modulators.

29. The cavity ringdown system recited in claim 22 further comprising:
   a cavity resonance photodetector,
   a polarized beam splitter and a quarter-wave plate capable of steering the entire reflected optical beam from the optical resonator onto the cavity resonance photodetector, said photodetector optically coupled to the beam splitter, the photodetector capable of receiving the reflected optical beam and converting the received beam to an electrical signal, and
   a laser-cavity locking loop electrically coupled to the photodetector, the laser-cavity locking loop capable of receiving the electrical signal and generating a feedback signal to maintain a lock between the optical-signal generator and the optical resonator.

30. The cavity ringdown system recited in claim 29 wherein the lock between the optical source and the optical cavity is maintained using the Pound-Drever-Hall technique.

31. The cavity ringdown system recited in claim 29 wherein the optical source includes an electro-optic modulator capable of providing RF sidebands to the optical beam.

32. The cavity ringdown system recited in claim 29 wherein the optical source generates an additional off-resonance continuous mode that is processed by the laser-cavity locking loop to maintain a lock between the optical source and the optical cavity.

33. The cavity ringdown system recited in claim 32 wherein the heterodyne detector is adapted to filter out contributions of the continuous mode to the heterodyne-beat waveform.

34. The cavity ringdown system recited in claim 22 wherein the chopping system chops the modes with respect to a chopping cycle that is suitable for the decay time characterizing the optical cavity when empty.

35. The cavity ringdown system recited in claim 22 wherein the optical cavity is adapted to contain a sample gas.

36. The cavity ringdown system recited in claim 22 wherein the cavity reflection photodetector includes a p-i-n diode in a resonant matching circuit.

37. The cavity ringdown system recited in claim 22 wherein the heterodyne photodetector includes a suitable detector, such as an avalanche photodiode, resonant matched p-i-n photodiode or photomultiplier.

38. The cavity ringdown system recited in claim 22 wherein the heterodyne photodetection system includes an RF demodulation component.

39. The cavity ringdown system recited in claim 22 wherein the optical source includes an adjustable power system capable of being responsive to increased intra-cavity absorption in the optical cavity for increasing power of the optical beam.

40. The cavity ringdown system recited in claim 22 wherein the chopping system is an adjustable chopping system capable of being responsive to increased intra-cavity absorption in the optical cavity by decreasing the duration of the chopping cycle.

41. A method of cavity ringdown spectroscopy including:
   providing for generation of an optical beam,
   providing for generation of a plurality of modes from the optical beam, the modes having a predetermined relative frequency offset,
   providing for out-of-phase chopping of the modes with respect to a chopping cycle such that the optical beam consists of only one dominant mode when incident upon an optical resonant cavity,
   providing for resonating of the modes in the cavity, and
   providing for heterodyne detection of an optical signal coupled out of the cavity, the optical signal including the modes, which modes overlap to produce a heterodyne-beat waveform, the heterodyne detection including:

providing for demodulation of the waveform to produce a heterodyne-beat amplitude, and providing for generation of a difference signal from adjacent chopping cycles of the heterodyne-beat amplitude.

42. The cavity ringdown spectroscopy method recited in claim 41 wherein providing for generation of an optical beam includes generating an intensity-stabilized continuous-wave laser beam.

43. The cavity ringdown spectroscopy method recited in claim 41 wherein providing for generation of an optical beam includes generation of an optical beam by a cw tunable laser.

44. The cavity ringdown spectroscopy method recited in claim 41 wherein providing for generation of an optical beam includes electro-optic modulation of the beam for providing RF sidebands to the optical beam.

45. The cavity ringdown spectroscopy method recited in claim 41 wherein providing for generation of a plurality of modes includes acousto-optic modulation of the beam into a plurality of modes having a relative frequency offset.

46. The cavity ringdown spectroscopy method recited in claim 41 wherein providing for generation of a plurality of modes includes providing a frequency offset to the modes that is related to the free-spectral range that characterizes the cavity.

47. The cavity ringdown spectroscopy method recited in claim 41 further comprising:

providing for coupling the reflected optical beam from the cavity to a transducer for providing an electrical signal in response to the reflected beam, and providing for locking between the optical-beam generation and the mode resonance.

48. The cavity ringdown spectroscopy method recited in claim 47 wherein providing for locking is performed using the Pound-Drever-Hall technique.

49. The cavity ringdown spectroscopy method recited in claim 47 wherein providing for generation of a plurality of modes includes generating an off-resonance continuous mode that is processed by the locking step.

50. The cavity ringdown spectroscopy method recited in claim 49 wherein the providing for heterodyne detection is adapted to filter out contributions of the continuous mode to the heterodyne-beat waveform.

51. The cavity ringdown spectroscopy method recited in claim 41 wherein the chopping cycle providing for out-of-phase chopping of the modes is suitable for the cavity decay time.

52. The cavity ringdown spectroscopy method recited in claim 41 wherein providing for resonating of the modes includes coupling the beam into a high-finesse cavity.

53. The cavity ringdown spectroscopy method recited in claim 41 wherein providing for resonating of the modes includes providing an intra-cavity sample gas having an absorption line to which at least one of the modes is tuned.

54. The cavity ringdown spectroscopy method recited in claim 41 wherein providing for heterodyne detection includes RF demodulation.

55. The cavity ringdown spectroscopy method recited in claim 41 wherein providing for generation of the beam includes increasing power to the beam in response to increased intra-cavity absorption in the cavity.

56. The cavity ringdown spectroscopy method recited in claim 41 wherein providing for out-of-phase chopping of the modes includes decreasing duration of the chopping cycle in response to increased intra-cavity absorption in the cavity.

* * * * *